(12) United States Patent
Nakatani et al.

(10) Patent No.: US 9,783,476 B2
(45) Date of Patent: Oct. 10, 2017

(54) METHOD OF PRODUCING 2'-TRIFLUOROMETHYL GROUP-SUBSTITUTED AROMATIC KETONE

(71) Applicant: Toray Fine Chemicals Co., Ltd., Tokyo (JP)

(72) Inventors: Jiro Nakatani, Moriyama (JP); Tatsuhiro Nozoe, Moriyama (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 15/126,692

(22) PCT Filed: Sep. 7, 2015

(86) PCT No.: PCT/JP2015/075314
§ 371 (c)(1),
(2) Date: Sep. 16, 2016

(87) PCT Pub. No.: WO2016/043079
PCT Pub. Date: Mar. 24, 2016

(65) Prior Publication Data
US 2017/0088499 A1    Mar. 30, 2017

(30) Foreign Application Priority Data
Sep. 19, 2014 (JP) ................ 2014-191327

(51) Int. Cl.
*C07C 45/42* (2006.01)
*C07C 49/80* (2006.01)

(52) U.S. Cl.
CPC .............. *C07C 45/42* (2013.01); *C07C 49/80* (2013.01)

(58) Field of Classification Search
CPC ..................................... C07C 45/42
USPC ........................................... 568/323
See application file for complete search history.

(56) References Cited

U.S. PATENT DOCUMENTS 5,969,188 A    10/1999 Hardwicke
2004/0077647 A1    4/2004 Cirillo et al.

FOREIGN PATENT DOCUMENTS

| CN | 102690180 | 9/2012 |
|---|---|---|
| CN | 102964233 | 3/2013 |
| JP | 2006-504667 A | 2/2006 |
| JP | 2009-102264 A | 5/2009 |
| JP | 2009-298715 A | 12/2009 |
| WO | 02/50009 A1 | 6/2002 |

OTHER PUBLICATIONS

J. L. Leazer et al., "An Improved Preparation of 3,5-Bis(trifluoromethyl)acetophenone and Safety Considerations in the Preparation of 3,5-Bis(trifluoromethyl)phenyl Grignard Reagent", *Journal of Organic Chemistry*, 2003, vol. 68, No. 9, pp. 3695-3698.
M. S. Maji et al., "Transition-Metal-Free Sonogashira-Type Coupling of ortho-Substituted Aryl and Alkynyl Grignard Reagents by Using 2,2,6,6-Tetramethylpiperidine-N-oxyl Radical as an Oxidant", *Organic Letters*, 2010, vol. 12, No. 17, pp. 3878-3881.
C. Benhaim et al., "Enantioselective Synthesis of β-Trifluoromethyl α-Amino Acids", *Organic Letters*, 2010, vol. 12, No. 9, pp. 2008-2011.
The First Office Action dated Mar. 28, 2017, of corresponding Chinese Application No. 201580009945.2, along with an English translation.
Zhou Yongqiang, et al., "Synthesis of m-Trifluoromethylacetophenone," Medical Industry Magazine, Dec. 31, 2000, pp. 79-80 with brief English abstract and partial translation of relevant portion.

*Primary Examiner* — Sikarl Witherspoon
(74) *Attorney, Agent, or Firm* — DLA Piper LLP (US)

(57) ABSTRACT

A method produces a 2'-trifluoromethyl-substituted aromatic ketone and includes reacting a 2-halogen-substituted benzotrifluoride compound with magnesium metal to convert the compound to a Grignard reagent; and reacting the Grignard reagent with an acid anhydride; and then hydrolyzing the resultant to produce a 2'-trifluoromethyl-substituted aromatic ketone. The method of producing a 2'-trifluoromethyl-substituted aromatic ketone enables 2'-trifluoromethyl-substituted aromatic ketone to be produced without using expensive raw materials by generating a Grignard reagent as an intermediate and reacting this Grignard reagent with an acid anhydride in an efficient productivity. The 2'-trifluoromethyl-substituted aromatic ketone that is produced by the method of producing a 2'-trifluoromethyl-substituted aromatic ketone can be used as fine chemicals, raw materials for pharmaceuticals and agrochemicals, raw materials for resins and plastics, electronics and information related materials, optical materials, and the like.

10 Claims, No Drawings

METHOD OF PRODUCING 2'-TRIFLUOROMETHYL GROUP-SUBSTITUTED AROMATIC KETONE

TECHNICAL FIELD

This disclosure relates to a method of producing a T-trifluoromethyl-substituted aromatic ketone, in particular, to an industrially superior method of producing a 2'-trifluoromethyl-substituted aromatic ketone.

BACKGROUND

2'-trifluoromethyl-substituted aromatic ketones are useful compounds for fine chemicals, raw materials for pharmaceuticals and agrochemicals, raw materials for resins and plastics, electronics and information related materials, optical materials, and the like. 2'-trifluoromethyl-substituted aromatic ketones are useful in industrial applications in a variety of fields.

As for a method of producing a 2'-trifluoromethyl-substituted aromatic ketone, trifluoromethyl benzoyl chloride is, in Japanese Patent Application Laid-Open Publication No. 2009-298715, coupled with ethyl magnesium chloride in the presence of an iron (III)-acetylacetonate catalyst followed by hydrolysis to thereby generate a 2'-trifluoromethyl-substituted aromatic ketone.

The method described in Japanese Patent Application Laid-Open Publication No. 2009-298715, however, uses expensive 2-trifluoromethyl benzoyl chloride (ALDRICH reagent catalog Japan 2012-2014 version: 25,600 yen/25 g) as a raw material and, therefore, the produced 2'-trifluoromethyl-substituted aromatic ketone ends up being expensive.

In Japanese Patent Application Laid-Open Publication No. 2009-102264, trifluoromethyl halogenated benzene is reacted with a vinyl ether in the presence of a palladium catalyst followed by hydrolysis to thereby generate a 2'-trifluoromethyl-substituted aromatic ketone.

The method described in Japanese Patent Application Laid-Open Publication No. 2009-102264 uses an expensive palladium catalyst and expensive DPPP (1,3-bis(diphenylphosphino)propane) as the catalyst's ligand and, therefore, the produced 2'-trifluoromethyl-substituted aromatic ketone ends up being expensive. In addition, it has been difficult to separate the palladium catalyst, the DPPP ligand, and the 2'-trifluoromethyl-substituted aromatic ketone.

In U.S. Pat. No. 5,969,188, trifluoromethyl benzoyl chloride is reacted with a secondary amine to generate trifluoromethyl benzamide as an intermediate. The resultant is reacted with a methylmagnesium Grignard reagent to thereby generate a 2'-trifluoromethyl-substituted aromatic ketone.

Further in U.S. Pat. No. 5,969,188, due to a route in which expensive 2-trifluoromethyl benzoyl chloride (ALDRICH reagent catalog Japan 2012-2014 version: 25,600 yen/25 g) is reacted with a secondary amine to thereby generate trifluoromethyl benzamide which is reacted with a methyl Grignard reagent, the process has been lengthy with operations being complicated. As a result, the obtained 2'-trifluoromethyl-substituted aromatic ketone has been expensive.

The above methods of producing a 2'-trifluoromethyl-substituted aromatic ketone have problems in their industrial use; and inexpensive methods of producing a 2'-trifluoromethyl-substituted aromatic ketone have thus been sought.

It could therefore be helpful to provide an industrially superior method of producing a 2'-trifluoromethyl-substituted aromatic ketone, which method uses inexpensive and readily-obtainable raw materials and exhibits high efficiency of production.

SUMMARY

We thus provide a method of producing a 2'-trifluoromethyl-substituted aromatic ketone comprising reacting a 2-halogen-substituted benzotrifluoride compound represented by general formula (1):

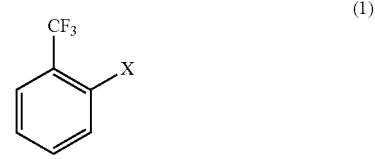

wherein X is Cl or Br, with magnesium metal to convert the compound to a Grignard reagent; and reacting the Grignard reagent with an acid anhydride; and then hydrolyzing the resultant to produce a 2'-trifluoromethyl-substituted aromatic ketone represented by general formula (2):

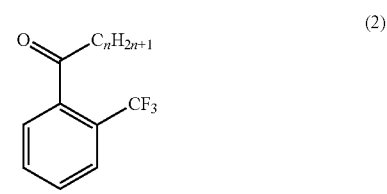

wherein n is an integer of 1 to 4.

The method of producing a 2'-trifluoromethyl-substituted aromatic ketone uses a relatively inexpensive 2-halogen-substituted benzotrifluoride compound (for example, 2-chlorobenzotrifluoride: ALDRICH reagent catalog Japan 2012-2014 version: 2,700 yen/100 g) as a starting substrate. Our method can generate a Grignard reagent as an intermediate without using an expensive raw material to produce a 2'-trifluoromethyl-substituted aromatic ketone by reacting this Grignard reagent with an acid anhydride in an efficient productivity. The method of producing a 2'-trifluoromethyl-substituted aromatic ketone is, therefore, an industrially superior production method.

The 2'-trifluoromethyl-substituted aromatic ketone that is produced by the method of producing a 2'-trifluoromethyl-substituted aromatic ketone can be used as fine chemicals, raw materials for pharmaceuticals and agrochemicals, raw materials for resins and plastics, electronics and information related materials, optical materials, and the like.

DETAILED DESCRIPTION

Our methods will be described in detail below.

The method of producing a 2'-trifluoromethyl-substituted aromatic ketone utilizes a 2-halogen-substituted benzotrifluoride compound represented by general formula (1) as a starting substrate:

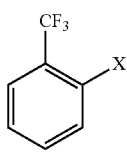

(1)

wherein X is Cl or Br.

Specific examples of the 2-halogen-substituted benzotrifluoride compound include o-chlorobenzotrifluoride and o-bromobenzotrifluoride.

The halogen atom of the 2-halogen-substituted benzotrifluoride compound is reacted with magnesium metal to convert the resulting compound to a Grignard reagent. A known conversion reaction can be used as the reaction for conversion to the Grignard reagent.

It is preferred that the magnesium metal be one in the form of powder.

The amount of magnesium metal used is preferably 0.8 to 3 times by mole as much as that of a raw material, 2-halogen-substituted benzotrifluoride compound.

It is preferred to add iodine, bromine, or an inexpensive compound containing them for the purpose of taking out an oxide film on the magnesium metal surface and increasing the reactivity. Preferred examples of such a compound include methyl iodide, methyl bromide, ethyl iodide, and ethyl bromide.

A reaction for conversion to a Grignard reagent is performed in a dehydrated system. For this reason, a solvent having in advance been dehydrated may be used for the reaction; or an inexpensive Grignard reagent may be added to a solvent before the reaction to remove water contained in the solvent.

As for a solvent for use in the Grignard reagent production, a solvent capable of efficiently promoting the reaction is employed. The solvent for use in the Grignard reagent production is preferably an ether solvent that allows the Grignard reagent to be readily generated. Specific examples of the solvent include diethyl ether, diisopropyl ether, tetrahydrofuran, N,N-dimethylformamide, N,N-dimethylacetamide, N-methylpyrrolidone, 1,3-dioxane, 1,4-dioxane, cyclopropyl methyl ether, methyl tertiary-butyl ether, ethylene glycol dimethyl ether, diethylene glycol dimethyl ether, triethylene glycol dimethyl ether, tetraethylene glycol dimethyl ether, benzene, toluene, and xylene. Of these, preferred is diethyl ether, diisopropyl ether, tetrahydrofuran, 1,3-dioxane, 1,4-dioxane, cyclopropyl methyl ether, and methyl tertiary-butyl ether.

Further, as for the amount of solvent used, it is preferred that the amount used be determined depending on the solubility or slurry concentration of the 2-halogen-substituted benzotrifluoride compound or Grignard reagent or the properties of a reaction solution. The amount of solvent used is preferably 1 to 100 times by mole as much as that of the 2-halogen-substituted benzotrifluoride compound. In one-fold by mole or less, the yield of the Grignard reagent may be low; and in 100 times by mole or more, the productivity may drop, which may results in a noneconomic process.

In the Grignard reagent production, LiCl (lithium chloride) is preferably made to coexist when 2-halogen-substituted benzotrifluoride compound represented by general formula (1):

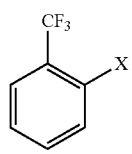

(1)

wherein X is Cl or Br,
is reacted with magnesium metal to convert the product to a Grignard reagent. That is because, by making LiCl to coexist, the Grignard reagent is promptly generated and the subsequent reaction of the reagent with an acid anhydride or alkylnitrile takes place in a high yield.

The amount of LiCl used is preferably 0.01 to 3 times by mole that of the 2-halogen-substituted benzotrifluoride compound. It is more preferred to be 0.05 to 1 times by mole. If the amount of LiCl is 0.01 to 3 times by mole that of the 2-halogen-substituted benzotrifluoride compound, generation of the Grignard reagent takes place more promptly and LiCl is fully dissolved in a reaction system.

Specific examples of the acid anhydride that is reacted with the Grignard reagent in the production method include acetic anhydride, propionic anhydride, butyric anhydride, and valeric anhydride. The acid anhydride reacted with the Grignard reagent in the production method is preferably acetic anhydride, propionic anhydride, or butyric anhydride.

The amount of the acid anhydride used is preferably 0.5 to 10 times by mole and more preferably 1 to 5 times by mole based on one mole of 2-halogen-substituted benzotrifluoride compound. If the amount is below 0.5 times by mole, an unreacted Grignard reagent may be left to lower the yield and the isolation and purification of an intended product may come to be more laborious. If the amount is above 10 times by mole, an unreacted acid anhydride may be left to decrease productivity and the separation of the unreacted acid anhydride from the 2'-trifluoromethyl-substituted aromatic ketone may come to be inefficient.

A solvent may be used in a reaction of a Grignard reagent with an acid anhydride. As for the solvent, preferred is a solvent that does not inhibit the reaction and can efficiently promote the reaction. Specific examples of the solvent include diethyl ether, diisopropyl ether, tetrahydrofuran, N,N-dimethylfounamide, N,N-dimethylacetamide, N-methylpyrrolidone, 1,3-dioxane, 1,4-dioxane, cyclopropyl methyl ether, methyl tertiary-butyl ether, ethylene glycol dimethyl ether, diethylene glycol dimethyl ether, triethylene glycol dimethyl ether, tetraethylene glycol dimethyl ether, benzene, toluene, and xylene. Of these, preferred is tetrahydrofuran, 1,3-dioxane, cyclopropyl methyl ether, benzene, toluene, xylene, and mesitylene.

The amount of the solvent used is preferably 0.05 to 50 times by weight as much as that of the 2'-trifluoromethyl-substituted aromatic ketone. When the amount of the solvent used is 0.05 times by weight or less, the heat of reaction may be hard to be removed, thereby making the reaction out of control. When it is 50 times by weight or more, productivity may be poor.

As a method of reacting a Grignard reagent with an acid anhydride, a solution containing an acid anhydride may be placed to a Grignard reagent solution or a Grignard reagent solution may be placed to a solution containing an acid anhydride. To prevent rapid generation of reaction heat or reaction runaway, it is preferred to adjust the rate of placing the solution while controlling the temperature in the reaction system such that the temperature is within a setting range by, for example, placing the solution placed continuously over time or intermittently in portions. A period of time required for the placement is preferably selected to be for 0.5 to 6 hours.

The reaction temperature for a Grignard reagent and an acid anhydride is preferably 0 to 100° C. and more preferably 10 to 50° C. If the reaction temperature is below 0° C., the reaction hardly progresses; and even if the reaction progresses it may stop midway. In addition, when above 100° C., the Grignard reagent may be broken down by heat before the reaction, which is not preferred.

The reaction time for a Grignard reagent and an acid anhydride is usually 0.5 to 40 hours at 0 to 100° C. after the entire volume of a Grignard reagent solution and a solution containing the acid anhydride are mixed.

A salt composed of a T-trifluoromethyl-substituted aromatic ketone and halogenated magnesium is formed after completion of the reaction of a Grignard reagent with an acid anhydride; and thus the hydrolysis of this salt produces the 2'-trifluoromethyl-substituted aromatic ketone. Water, acidic water, or alkaline water is preferably added to the reaction solution at the completion of the reaction to hydrolyze the salt composed of the 2'-trifluoromethyl-substituted aromatic ketone and halogenated magnesium. Preferred is a method comprising removing the generated halogenated magnesium in a water phase and subsequently isolating the 2'-trifluoromethyl-substituted aromatic ketone from the obtained oil phase.

A 2'-trifluoromethyl-substituted aromatic ketone to be produced is represented by general formula (2):

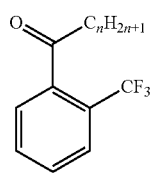

(2)

wherein n is an integer of 1 to 4.

The 2'-trifluoromethyl-substituted aromatic ketone to be produced is preferably 2'-trifluoromethyl acetophenone, 2'-trifluoromethyl propiophenone, and 2'-trifluoromethyl butyrophenone.

Examples of a method of isolating an intended 2'-trifluoromethyl-substituted aromatic ketone from the reaction solution include a distillation method, a crystallization method, an extraction method, column separation by silica or the like, and a simulated moving bed adsorption separation method; and two or more of these methods may be combined. For example, with regard to the distillation method, preferred are simple distillation, rectification, distillation under reduced pressure, and distillation under atmospheric pressure; and distillation under reduced pressure is more preferably used.

Because the 2'-trifluoromethyl-substituted aromatic ketone that is obtained by the production method is a compound that is useful in a variety of fields, it is significant that this compound can be industrially obtained in an efficient productivity.

EXAMPLES

By way of examples, our methods will be further described in detail below. It is to be noted that the manufacturer grade of all reagents used here is a level equivalent to grade 1 or better.

Example 1

To a 200 ml-four-necked flask with a thermometer, 75.0 g of tetrahydrofuran (1.04 mol; manufactured by Nacalai Tesque, Inc.), 5.1 g of magnesium powder (0.208 mol; manufactured by Chuo-kosan), 1.7 g of LiCl (0.04 mol; manufactured by Nacalai Tesque, Inc.) were placed and the mixture was stirred while the inside of the system was substituted with a nitrogen gas. To this, 0.5 g of 1 mol/L ethylmagnesium bromide THF solution (manufactured by Tokyo Chemical Industry Co., Ltd.) was added and water in the system removed. Subsequently, 0.44 g of ethyl bromide (0.004 mol; manufactured by Wako Pure Chemical Industries, Ltd.) was added thereto. The mixture was stirred for a while; and the generation of heat confirmed Subsequently, 36.1 g of o-chlorobenzotrifluoride (0.2 mol; manufactured by Wako Pure Chemical Industries, Ltd.) was gradually added dropwise, while the temperature of the reaction solution was kept at 45 to 50° C. After completion of the dropwise addition, the mixture was allowed to mature while stirred at 45° C. for five hours, thereby obtaining a Grignard reagent solution.

Next, to a 200 ml-four-necked flask with a thermometer, 30.6 g of acetic anhydride (0.3 mol; manufactured by Wako Pure Chemical Industries, Ltd.), 10.8 g of toluene (0.3 fold by weight/o-chlorobenzotrifluoride: manufactured by Wako Pure Chemical Industries, Ltd.) were placed and the mixture stirred in a water bath while the inside of the system was substituted with a nitrogen gas. To this, the above Grignard reagent solution was added dropwise while the temperature of the reaction solution was controlled to be 20 to 30° C. The entire volume of the Grignard reagent solution was added dropwise and then the mixture stirred at 25° C. for two hours.

After completion of stirring, the temperature of the reaction solution was decreased to room temperature; and 39.2 g of 3% hydrogen chloride aqueous solution was gradually added dropwise thereto in a water bath. After the dropwise addition, the hydrolysis was completed by stirring for one hour. After the hydrolysis, the stirring was stopped and the resultant left to stand for separation, thereby obtaining an oil phase containing o-trifluoromethyl acetophenone.

The obtained oil phase was analyzed by a gas chromatography method (GC) and, as a result, the yield of 2'-trifluoromethyl acetophenone reaction was 82.7% (based on the raw material, o-chlorobenzotrifluoride).

Example 2

A reaction was carried out in the same manner as described in Example 1 except that 36.1 g (0.2 mol) of o-chlorobenzotrifluoride was altered to 45.0 g (0.2 mol) of o-bromobenzotrifluoride in Example 1.

The obtained oil phase was analyzed by a gas chromatography method and, as a result, the yield of T-trifluoromethyl acetophenone reaction was 85.5% (based on the raw material, o-bromobenzotrifluoride).

Example 3

A reaction was carried out in the same manner as described in Example 1 except that 30.6 g (0.3 mol) of acetic anhydride was altered to 39.0 g (0.3 mol) of propionic anhydride in Example 1. The obtained oil phase was analyzed by a gas chromatography method and, as a result, the yield of 2'-trifluoromethyl propiophenone reaction was 73.3% (based on the raw material, o-chlorobenzotrifluoride).

Example 4

A reaction was carried out in the same manner as described in Example 1 except that 30.6 g (0.3 mol) of acetic anhydride was altered to 47.8 g (0.3 mol) of butyric anhydride in Example 1. The obtained oil phase was analyzed by a gas chromatography method and, as a result, the yield of 2'-trifluoromethyl butyrophenone reaction was 74.5% (based on the raw material, o-chlorobenzotrifluoride).

Example 5

A reaction was carried out in the same manner as described in Example 1 except that LiCl was not added in Example 1. The obtained oil phase was analyzed by a gas chromatography method and, as a result, the yield of 2'-trifluoromethyl acetophenone reaction was 63.4% (based on the raw material, o-chlorobenzotrifluoride).

Example 6

The oil phase obtained in Example 1 was subjected to distillation under reduced pressure (the degree of reduced pressure: 0.4 to 1.3 kPa; the temperature of distillation: 95 to 100° C.) to yield 2'-trifluoromethyl acetophenone with a GC purity of 98.7% in a total yield of 72.4% (based on the raw material, o-chlorobenzotrifluoride).

Example 7

The oil phase obtained in Example 3 was subjected to distillation under reduced pressure (the degree of reduced pressure: 0.4 to 1.3 kPa; the temperature of distillation: 105 to 110° C.) to yield 2'-trifluoromethyl propiophenone with a GC purity of 98.0% in a total yield of 66.0% (based on the raw material, o-chlorobenzotrifluoride).

Comparative Example 1

A reaction was carried out in the same manner as described in Example 1 except that 36.1 g (0.2 mol) of o-chlorobenzotrifluoride was altered to 45.0 g (0.2 mol) of m-bromobenzotrifluoride in Example 1. The obtained oil phase was analyzed by a gas chromatography method and, as a result, the yield of 3'-trifluoromethyl acetophenone reaction was 38.1% (based on the raw material, m-bromobenzotrifluoride).

Comparative Example 2

A reaction was carried out in the same manner as described in Comparative Example 1 except that 45.0 g (0.2 mol) of m-bromobenzotrifluoride was altered to 45.0 g (0.2 mol) of p-bromobenzotrifluoride in Comparative Example 1. The obtained oil phase was analyzed by a gas chromatography method and, as a result, the yield of 4'-trifluoromethyl acetophenone reaction was 40.0% (based on the raw material, p-bromobenzotrifluoride).

Comparative Example 3

A reaction was carried out in the same manner as described in Comparative Example 2 except that 30.6 g (0.3 mol) of acetic anhydride was altered to 39.0 g (0.3 mol) of propionic anhydride in Comparative Example 2. The obtained oil phase was analyzed by a gas chromatography method and, as a result, the yield of 4'-trifluoromethyl propiophenone was 34.5% (based on the raw material, p-bromobenzotrifluoride).

INDUSTRIAL APPLICABILITY

Our method of producing a 2'-trifluoromethyl-substituted aromatic ketone enables 2'-trifluoromethyl-substituted aromatic ketone to be produced without using expensive raw materials by generating a Grignard reagent as an intermediate and reacting this Grignard reagent with an acid anhydride in an efficient productivity. The method of producing a 2'-trifluoromethyl-substituted aromatic ketone is an industrially superior production method.

The 2'-trifluoromethyl-substituted aromatic ketone that is produced by the method of producing a 2'-trifluoromethyl-substituted aromatic ketone can be used as fine chemicals, raw materials for pharmaceuticals and agrochemicals, raw materials for resins and plastics, electronics and information related materials, optical materials and the like.

What is claimed is:

1. A method of producing a 2'-trifluoromethyl-substituted aromatic ketone comprising reacting a 2-halogen-substituted benzotrifluoride compound represented by general formula (1):

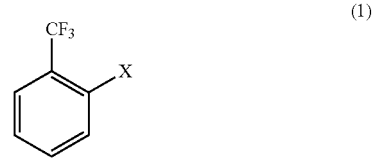

wherein X is Cl or Br
with magnesium metal in the presence of LiCl to convert the compound to a Grignard reagent;
and reacting said Grignard reagent with an acid anhydride; and then hydrolyzing the resultant to produce a 2'-trifluoromethyl-substituted aromatic ketone represented by general formula (2):

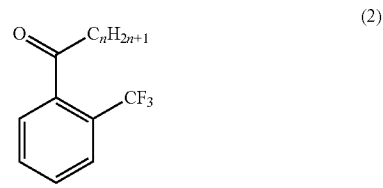

wherein n is an integer of 1 to 4.

2. The method according to claim 1, wherein said acid anhydride is acetic anhydride, propionic anhydride, or butyric anhydride.

3. The method according to claim 1, wherein said 2'-trifluoromethyl-substituted aromatic ketone is 2'-trifluoromethyl acetophenone, 2'-trifluoromethyl propiophenone, or 2'-trifluoromethyl butyrophenone.

4. The method according to claim 1, wherein when said 2-halogen-substituted benzotrifluoride compound represented by general formula (1):

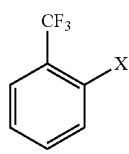

(1)

wherein X is Cl or Br is reacted with said magnesium metal in the presence of lithium chloride to convert the compound to said Grignard reagent.

5. The method according to claim 4, wherein the amount of said lithium chloride is 0.01 to 3 times by mole that of said 2-halogen-substituted benzotrifluoride compound.

6. The method according to claim 2, wherein said 2'-trifluoromethyl-substituted aromatic ketone is 2'-trifluoromethyl acetophenone, 2'-trifluoromethyl propiophenone, or 2'-trifluoromethyl butyrophenone.

7. The method according to claim 2, wherein when said 2-halogen-substituted benzotrifluoride compound represented by general formula (1):

(1)

wherein X is Cl or Br is reacted with said magnesium metal in the presence of lithium chloride to convert the compound to said Grignard reagent.

8. The method according to claim 3, wherein when said 2-halogen-substituted benzotrifluoride compound represented by general formula (1):

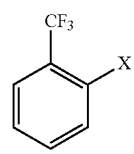

(1)

wherein X is Cl or Br is reacted with said magnesium metal in the presence of lithium chloride to convert the compound to said Grignard reagent.

9. The method according to claim 7, wherein the amount of said lithium chloride is 0.01 to 3 times by mole that of said 2-halogen-substituted benzotrifluoride compound.

10. The method according to claim 8, wherein the amount of said lithium chloride is 0.01 to 3 times by mole that of said 2-halogen-substituted benzotrifluoride compound.

* * * * *

UNITED STATES PATENT AND TRADEMARK OFFICE
CERTIFICATE OF CORRECTION

PATENT NO. : 9,783,476 B2  
APPLICATION NO. : 15/126692  
DATED : October 10, 2017  
INVENTOR(S) : Nakatani et al.

Page 1 of 1

It is certified that error appears in the above-identified patent and that said Letters Patent is hereby corrected as shown below:

In the Specification

In Column 1
At Line 8, please change "T-tri-" to -- 2'-tri- --.

In Column 5
At Line 18, please change "T-trifluoromethyl-substituted" to -- 2'-trifluoromethyl-substituted --.

Signed and Sealed this
Thirteenth Day of March, 2018

Andrei Iancu
*Director of the United States Patent and Trademark Office*